(12) United States Patent
Hood

(10) Patent No.: US 7,082,632 B2
(45) Date of Patent: Aug. 1, 2006

(54) COLLAPSIBLE, EXTENDABLE, TRACTION-PROVIDING, PORTABLE RESCUE DEVICE

(76) Inventor: Thomas W. Hood, 205 Monument Rd., Hinsdale, NH (US) 03451

( * ) Notice: Subject to any disclaimer, the term of this patent is extended or adjusted under 35 U.S.C. 154(b) by 0 days.

(21) Appl. No.: 10/739,255

(22) Filed: Dec. 18, 2003

(65) Prior Publication Data

US 2004/0128767 A1    Jul. 8, 2004

Related U.S. Application Data

(60) Provisional application No. 60/434,454, filed on Dec. 18, 2002.

(51) Int. Cl.
*A47B 1/00* (2006.01)

(52) U.S. Cl. .................... 5/625; 5/627; 5/628

(58) Field of Classification Search ............ 5/625–629, 5/111, 114
See application file for complete search history.

(56) References Cited

U.S. PATENT DOCUMENTS

| | | | | |
|---|---|---|---|---|
| 3,566,422 A | * | 3/1971 | Klippel | 5/627 |
| 3,611,454 A | * | 10/1971 | Klippel | 5/625 |
| 3,707,734 A | * | 1/1973 | Matthews | 5/628 |
| 3,732,863 A | * | 5/1973 | Harrington | 602/19 |
| 5,274,864 A | * | 1/1994 | Morgan | 5/627 |
| 5,414,883 A | * | 5/1995 | Fangrow, Jr. | 5/625 |
| 5,819,746 A | * | 10/1998 | Walton | 128/869 |

\* cited by examiner

*Primary Examiner*—Michael Trettel

(74) *Attorney, Agent, or Firm*—George W. Dishong

(57) ABSTRACT

Disclosed herein is a collapsible, convertible, extendable, traction-providing, portable stretcher/body splint type rescue device for use generally in emergency rescue field situations and having three main parts: a top or head portion, a middle or body portion, and an optional bottom or foot portion, all of which are formed from radiolucent material. The rescue device of the present invention further includes a head gear portion that is slidably adjustable, can provide dynamic cervical traction in the field, and is positioned on, yet easily removable from, the top or head portion. There is also padding on the top and middle portions which is removable, as well as a plurality of restraining devices such as webs, gores, straps and flaps to immobilize a victim on the rescue device.

58 Claims, 4 Drawing Sheets

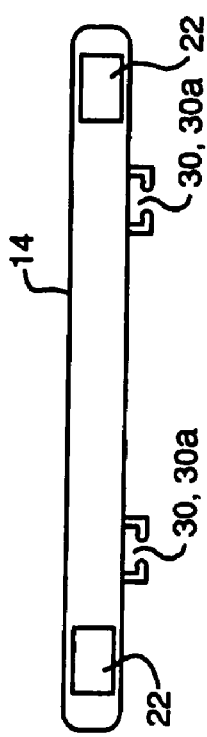
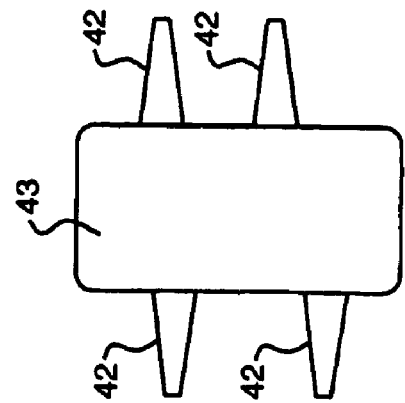
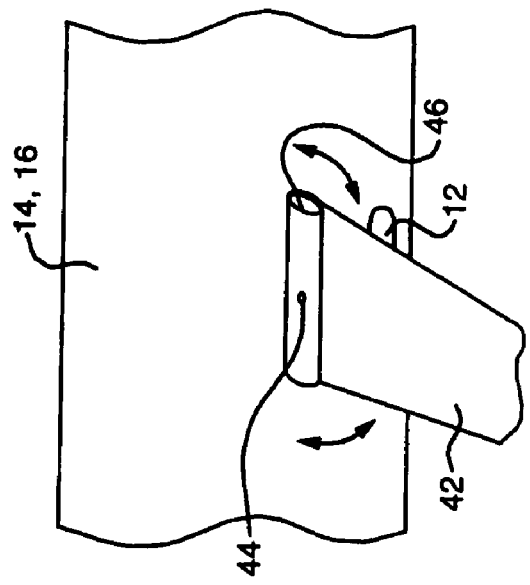
FIG. 3
FIG. 4
FIG. 4A

COLLAPSIBLE, EXTENDABLE, TRACTION-PROVIDING, PORTABLE RESCUE DEVICE

CROSS REFERENCES TO RELATED APPLICATION

This Application claims priority to the Provisional Application of the same title: Collapsible, Extendable, Traction-Providing, Portable Rescue Device. The Provisional Ser. No. is 60/434,454 filed on Dec. 18, 2002, confirmation # 6170.

STATEMENT AS TO RIGHTS TO INVENTIONS MADE UNDER FEDERALLY SPONSORED RESEARCH AND DEVELOPMENT

Not applicable

FIELD OF THE INVENTION

The invention relates to stretchers usable in the field for emergency rescue. More particularly the invention relates to multi-purpose rescue stretchers that are collapsible and light-weight. Most particularly the invention relates to a light-weight, collapsible stretcher that is easily packable, saves space, and has multiple uses including being able to provide dynamic traction for the neck vertebrae while in the field, and also provide virtually complete immobilization of an injured victim, including even animals.

BACKGROUND OF THE INVENTION

Presently there are many different types of stretchers available for use in the field—for example at the site of an automobile or skiing accident or military operation. Particularly in field conditions, improvised emergency devices must be used for victims because special equipment suitable for every unique situation is simply not available.

While it would be desirable to have specialized and precisely-adapted rescue and transportation devices available at all times for every emergency, whether in a city, country, military action, water, snow, ice, gullies, cliffs, vehicles etc., such is usually not the case. Whatever is on hand is used.

Additionally, while there are many types of stretchers in existence none really suites all of the possible applications. For example, a conventional stretcher is generally 18 inches wide×72 inches long, comes in one, solid piece and is called a "long board" stretcher. There are also 32 inch long "short board" stretchers available, for use for example, in removing a victim from a vehicle. In fact, most ambulances are required to carry both a 72 inch "long board" and a 32 inch "short board". This two-board arrangement presents several problems. The main problem is that, especially in the case of a possible spinal injury, if a person is first extricated from the vehicle using a 32 inch short board, that person, once extricated, will have to then be moved onto a full length 72 inch long board for transport. Such multiple handling of the victim increases the chance for permanent damage to the victim, especially in the case of a spinal injury. In addition, rescuers must carry two different types of boards, each one only useful for certain limited purposes. The 32 inch short board is useful for extrication, but doesn't stabilize the whole body and is not used for transport. The 72 inch long board stabilizes the body to some extent but is often too large to fit into many places where a victim is found and is awkward to carry. In a case for example with a small ravine or vehicle, only the short board can be carried in to the victim initially, then the victim must be carried out in a less than desirable position on the shot board before transfer can be made to the 72 inch long board.

Another example in which current stretchers are not ideal is the skiing industry. Because most stretchers are 18 inches wide and not all ski patrol sleds are 18 inches wide, many conventional stretchers are too wide to fit in the sleds used by ski patrollers to bring injured people off a mountain. Thus the patient may not be put on a stretcher initially, and will have to be moved to a stretcher once he is brought off the mountain.

A further area where current stretchers are not ideal is in military operations. Often a medic will have to go to the victim without a stretcher because conventional stretchers are too big to be carried, for example, on the back of a medic, especially during a parachute jump. Additionally, only so many large stretchers can be carried in a helicopter. Finally, carrying conventional stretchers occupies the rescuer's hands, thus limiting what else the rescuer can carry and operate.

Another problem with conventional stretchers and the current state of the art is that while conventional stretchers are padded to protect the victim the padding is essentially permanently attached to the stretcher. This non-removable padding prevents easy thorough cleaning of the stretcher. The padding is cleaned as well as possible while remaining on the stretcher. The same is true for most padding used to cushion the head of a victim. It is non-removable and not easily cleaned. Cleaning rescue and transport equipment after serious injuries, especially where blood and other bodily fluids have soiled the padding, is especially crucial today to prevent the spread of AIDS and other new diseases.

A further shortfall of current stretchers for use in the field is that while most are able to provide basic stabilization for the head and spine of the victim, they can not provide traction to the spine of the victim in the field to prevent further spinal injury during rescue and transport. Generally when a body is immobilized, for example on a stretcher, a certain amount of movement of the skeletal structure relative to the body envelope in response to acceleration forces (both positive and negative) during rescue and transport can not be avoided. But, it is desirable that the entire skeletal structure, including the skull, move together if they are going to move. Of course all such movement should be kept to a minimum, and this is particularly important with cervical spine injuries. However, with conventional stretcher restraint devices, the restraint devices are attached over the skin of the victim, and the head is immobilized, thus leaving the skeletal structure movable within the skin envelope while the skull is not able to move with the rest of the skeletal structure, thus creating risk for additional injury during rescue and transport. Such movement of the victim's skeletal structure happens mostly due to the gravity force vector.

Normally the position of a victim on a stretcher is supine, with the body resting on a rigid base—i.e. the stretcher. However, it is often necessary to tilt the stretcher during rescue, either by rotation around the longitudinal axis of the stretcher or in the vertical plane of the spine. For example, in the case of a victim vomiting the stretcher and victim would have to be turned on his/her side to keep the victim's airway open.

It is also often necessary to tilt or turn the stretcher to negotiate inclines, stairways, narrow passageways, etc. Thus the means by which the victim is attached or strapped to the stretcher must be able to resist snagging and be secure enough to keep the victim on the stretcher. Yet it is also essential that any rotating and/or tilting which changes the gravity force vector relative to the spinal axis does not cause appreciable tensional or compressive forces on the spine or neck due to the weight of the head and body during such rotating and/or tilting.

As the skeletal structure shifts within the body envelope in response to all the forces, the spatial relationship of the skull to the rest of the skeleton must be maintained, especially in the case of spinal injuries. However, as noted above, most conventional stretchers do not prevent movement of the skeleton with respect to the skin envelope, even if the head is immobilized, thus leaving the victim open to possible additional injury from the skeletal structure moving while the skull is immobilized.

There is, however, at least one stretcher currently available that can provide traction to the spine in the field, but the device, disclosed in U.S. Pat. No. 3,732,863 to Harrington, suffers from other shortfalls noted above. For example, the padding for the head and body is non-removable and the stretcher is a one-piece conventional 72 inch length. Thus, while the Harrington device can provide traction, the stretcher does not fit into every location and a patient may still have to be transported to some extent on a 32 inch conventional short board first and risk additional spinal or other damage from being transferred between the short board used for immediate rescue and the Harrington board used for transport.

Additionally, many conventional stretchers are made of wood that is heavy, can not be x-rayed and can absorb bodily fluids which is highly undesirable in these days of AIDS and other dangerous bodily-fluid borne viruses.

Thus, it would be desirable to have a light-weight, totally portable, collapsible yet extendable rescue device that can fully and completely stabilize a victim and provide cervical traction in the field. It would also be desirable to have a rescue device that can be used all the way from initial rescue to transport to emergency room and x-ray without having to transfer the victim to multiple stretchers, beds, etc. before the extent of the victim's injuries is determined. In addition, it would be desirable to have a stretcher or rescue device that has padding that is easily removable and washable such that both the stretcher and padding can be easily and completely cleaned.

SUMMARY OF THE INVENTION

A most basic embodiment of the invention is a collapsible, extendable, traction providing, portable stretcher type rescue device having three main parts: a top or head portion, a middle or body portion, and an optional bottom or foot portion, all of which are formed from radiolucent material. The rescue device of the present invention further includes a head gear portion that is slidably adjustable and can provide dynamic cervical traction in the field, and is positioned on, yet easily removable from, the top or head portion. There is also padding on the top and middle portions which is removable, as well as a plurality of restraining devices such as webs, gores, straps and flaps to immobilize a victim on the rescue device.

An example embodiment may have a top or head portion, a middle portion and an optional bottom or foot portion. The maximum width of the rescue device of the present invention may vary, being any desirable and/or functional width depending on the exact application for which the device will be used—for example, ski patrol, military or general rescue.

Because the invention is formed in three separate but attachable sections, one single device can be used or formed in three different lengths to suit various rescue scenarios. For example, the entire device could be packaged and carried on the back of a medic being dropped from a helicopter, or carried on one's back to the site of an automobile accident, wherein upon arrival at the victim, the top or head portion could be used to stabilize a victim while he/she is extricated from a vehicle, then once the victim is out of the vehicle, the middle section could be attached, without further moving the victim, to form a single long board on which to transport the victim. The bottom or foot portion would be attachable as desired depending on the height of the victim.

Conventional practice requires a transfer of a victim from a 32 inch board on which the victim is extracted, to a 72 inch board to transport the victim, thus risking aggravating existing injuries or causing additional injuries during the transfer between boards/stretchers. In fact, often the trauma caused by an accident or initial injury is exacerbated during subsequent transfer and transport of a victim.

The present invention minimizes additional trauma by eliminating a common and, until now, necessary transfer from short board to long board. In addition, with its removable, adjustable head gear portion, the nature and orientation of its body restraining devices, removable head and body padding and its two or three-part structure, the present invention allows for complete immobilization of a victim with no transfer between stretchers. The invention also provides cervical traction while in the field and during transport such that the relationship of the skull to the rest of the skeletal structure is maintained during rescue and transport so as to minimize or eliminate additional injury due to rescue and transport. The collapsible/convertible device of the present invention is usable from initial rescue scene to x-ray room with no further movement of the victim after the victim is secured on the invention.

Thus, one aspect of the invention is to provide a collapsible or convertible multi-part rescue device that is assemblable into a full size stretcher-type rescue device.

Another aspect of the invention is to provide a light-weight, space-saving rescue device that can be stowed in smaller spaces than conventional stretchers, and can be packaged to be easily carried by a rescue person and carried so as to leave the rescuer's hands free, for example packaged in a back-pack type assembly for transport to the rescue site.

A further aspect of the invention is to provide one rescue device that can be used in several different forms, for example a short form, a long form, and an optional extended form.

An additional aspect of the invention is to provide an easily disassemblable and washable rescue device, with removable and washable padding.

A still further aspect of the invention is to provide a rescue device that can apply dynamic traction in the field, to almost completely immobilize a victim—by immobilizing the skeletal structure yet allowing the skull to move with any amount of skeletal motion that may occur.

Yet another aspect of the invention is to provide a rescue device that can be used for every step of a rescue from initial extrication, to transport, to emergency room and x-ray, without having to transfer a victim between, for example, short and long stretcher boards.

An additional aspect of the invention is to provide a rescue device that may be formed at any desired width to suit the application for which it is used, for example ski rescue, military applications including search and rescue, and general civilian emergency services.

These and other aspects of the invention will become obvious to one of ordinary skill in the art upon review of the following detailed description, and accompanying figures.

BRIEF DESCRIPTION OF THE DRAWING FIGURES

FIG. 3 is an end view of the top/head section showing example receiving tracks for the rails, and showing the receiving portions used to connect the top/head section to the middle/body section of the device.

FIG. 4 is an example illustration showing a method by which a web/flap/gore may be rotatably attached to the device.

FIG. 4a shows the webs/flaps/gores attached to the underside of the removable padding.

DETAILED DESCRIPTION OF THE INVENTION

Figure 1:
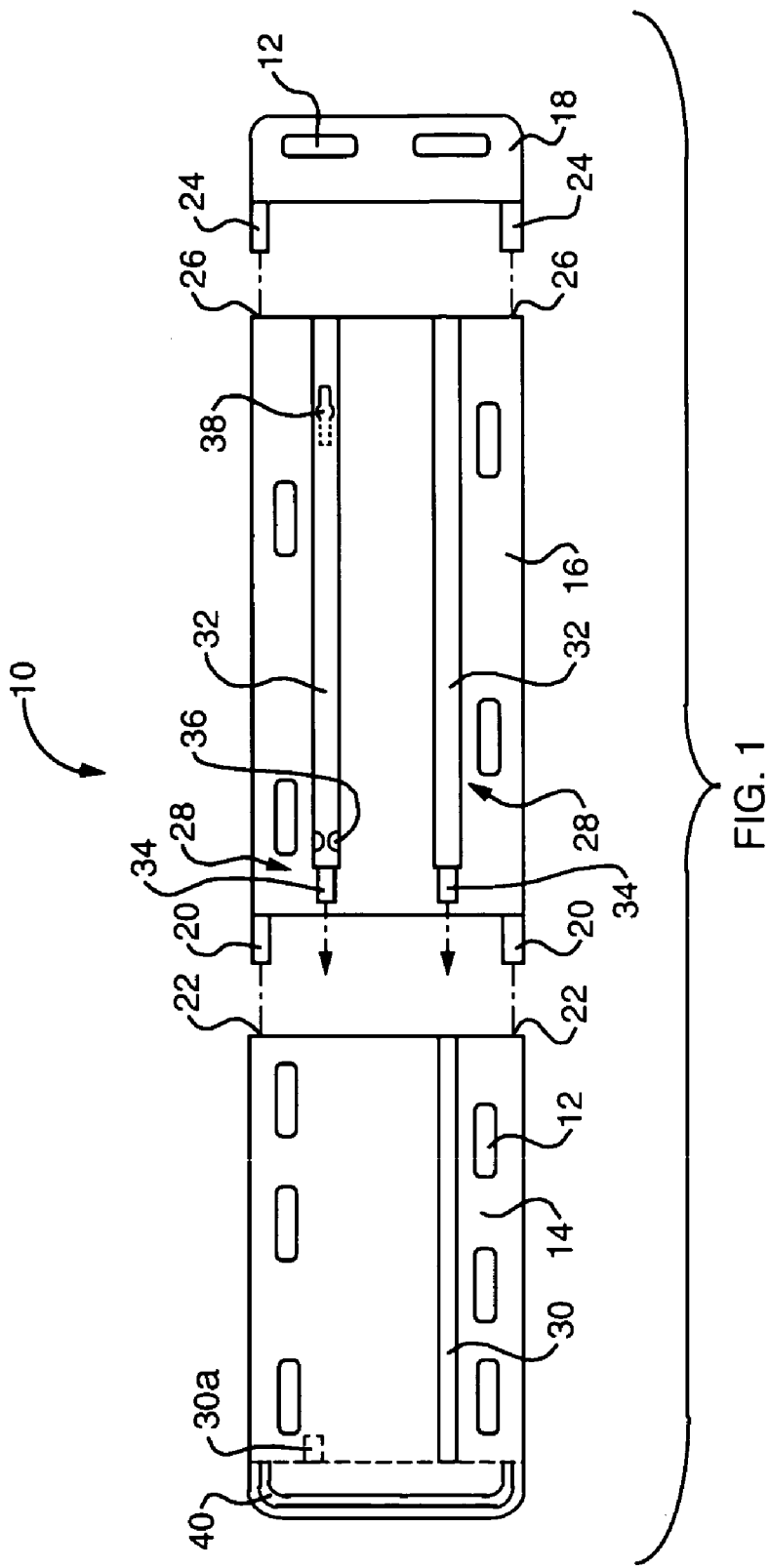
FIG. 1 is a bottom view of the rescue device of the present invention shown with the three main sections separated, and showing the rails on the underside of the device.

Referring now to the drawing figures, in which like reference numerals refer to like elements throughout, a most basic embodiment of the invention is a collapsible, convertible, extendable, traction-providing, portable stretcher type rescue device having three main parts: a top or head portion, a middle or body portion, and an optional bottom or foot portion, all of which are preferably formed from radiolucent material. The rescue device of the present invention further includes a head gear portion that is slidably adjustable, can provide dynamic cervical traction in the field, and is positioned on, yet easily removable from, the top or head portion. There is also padding on the top and middle portions which is removable, as well as a plurality of restraining devices such as webs, gores, straps and flaps to immobilize a victim on the rescue device.

Referring now to FIG. 1 the device 10 of the present invention is preferably made of radiolucent material (as are all parts of the device 10) to facilitate the taking of X-ray photographs in the position of arrival at the hospital or other medical center. The device 10 can be formed by injection molding, thus can be hollow and have a foam type core material blown or otherwise inserted within the hollow device. A plurality of hand holds 12 provide means for carrying the device 10. Device 10 is comprised of two main sections: a top or head portion 14 and a middle or body portion 16 which are assemblable together to form one continuous surface if desired. There is also an optional bottom or foot section 18 which allows for the length of the overall device 10 to be extended.

Top or head portion 14 is preferably of a shorter length than middle or body portion 16 such that top portion 14 may be used in initial extrication, stabilization and rescue of a victim, and then middle/body portion 16 attached to form a complete body support for the victim. For example, top/head portion 14 may be in the range of about 30–34 inches in length and middle/body portion 16 may be in the range of about 38–42 inches in length to provide a combined length in the range of about 68–76 inches for the top/head portion 14 and middle/body portion 16 when attached together. Optional bottom/foot portion 18 may be in the range of about 4–8 inches in length for a total length in the range of about 72 inches to about 84 inches.

Top/head portion 14 and middle/body portion 16 may be attached in a number of ways. For example, as shown in FIG. 1, middle/body portion 16 may have an attachment extension 20 at each edge which slidably fit into a receiving portion 22 at each edge of top/head portion 14 to create a single flush surface. Similarly, bottom/foot portion 18 may have an attachment extension 24 at each edge which fit slidably into a receiving portion 26 at each edge of middle/body portion 14 to form a single flush surface of greater length with top/head portion 14, middle/body portion 16 and bottom/foot portion 18 all connected than when only top/head portion 14 and middle/body portion 16 are attached together. However, attachment of bottom/foot portion 18 is optional and whether it is used or not would depend on the height of the victim, if greater length is needed. FIG. 3 illustrates receiving portions 22 for example in top/head portion 14 and/or middle/body portion 16.

Device 10 is also provided with a means to elevate device 10 above a surface on which device 10 is resting, such that device 10 may be easily picked up from a surface. Such means may include telescoping rails 28 which are affixed to the bottom surface of middle/body portion 16 and which are extendable below and along the bottom surface of top/head portion 14. Shown in FIGS. 1 and 3 is an example of two tracks 30 that may used to secure rails 28 in place once extended. Rails 28 may be secured in an extended position in a number of ways such as by sliding into track mechanism 30 that is located along the bottom surface of top/head portion 14; by insertion into a receiving device 30a such as a lock or clamp located on the bottom surface of top/head portion 14, shown towards the top of FIG. 1 and which is also shown in FIG. 3; or by being formed with a locking mechanism on the telescoping rails 28 themselves, for example a telescoping and locking mechanism as is found on many vacuum cleaner handles and umbrella handles, with which there would be no corresponding attachment device located on top/head portion 14, as shown in FIG. 1.

For example, if rails 28 have two telescoping parts, an outer part or rail 32 and an inner part or rail 34, a small aperture or apertures 36 would be located at one (near) end of the outer part 32 and a spring-type mechanism 38 could be located at one (far) end of the inner part 34. Normally the spring-type mechanism 38 is compressed when the inner part 34 is contained within the outer part 32, but such that when the inner part 34 is fully extended and the spring-type mechanism 38 passes the aperture(s) 36 compression on the spring-type mechanism 38 is released and the spring-type mechanism 38 extends into and fills the aperture(s) 36. With spring-type mechanism 38 lodged in aperture 36 the inner part 34 can not be moved/slid back into the outer part 32 unless or until the spring-type mechanism 38 is compressed, for example by a rescue worker, and the inner part 34 moved such that the spring-type mechanism 38 is no longer aligned with the aperture(s) 36 and the inner part 34 may then be slid back inside the outer part 32.

In FIG. 1 all three examples of ways that rails 28 could be received and/or secured in an extended position are shown. However all three example methods shown on one Figure are for example only. Preferably only one method of securing extended rails 28 in place would be used on any one device 10. Three example methods are shown on one device 10 for illustrative purposes only, to show that there may be several ways to manufacture, locate and design rails 28 to elevate device 10 from a surface for ease of picking up device 10 with a victim secured thereon. FIG. 1 also illustrates an optional reinforcing member 40 that may be located around the perimeter of each of the top, middle and bottom portions to strengthen and reinforce device 10.

Figure 2:
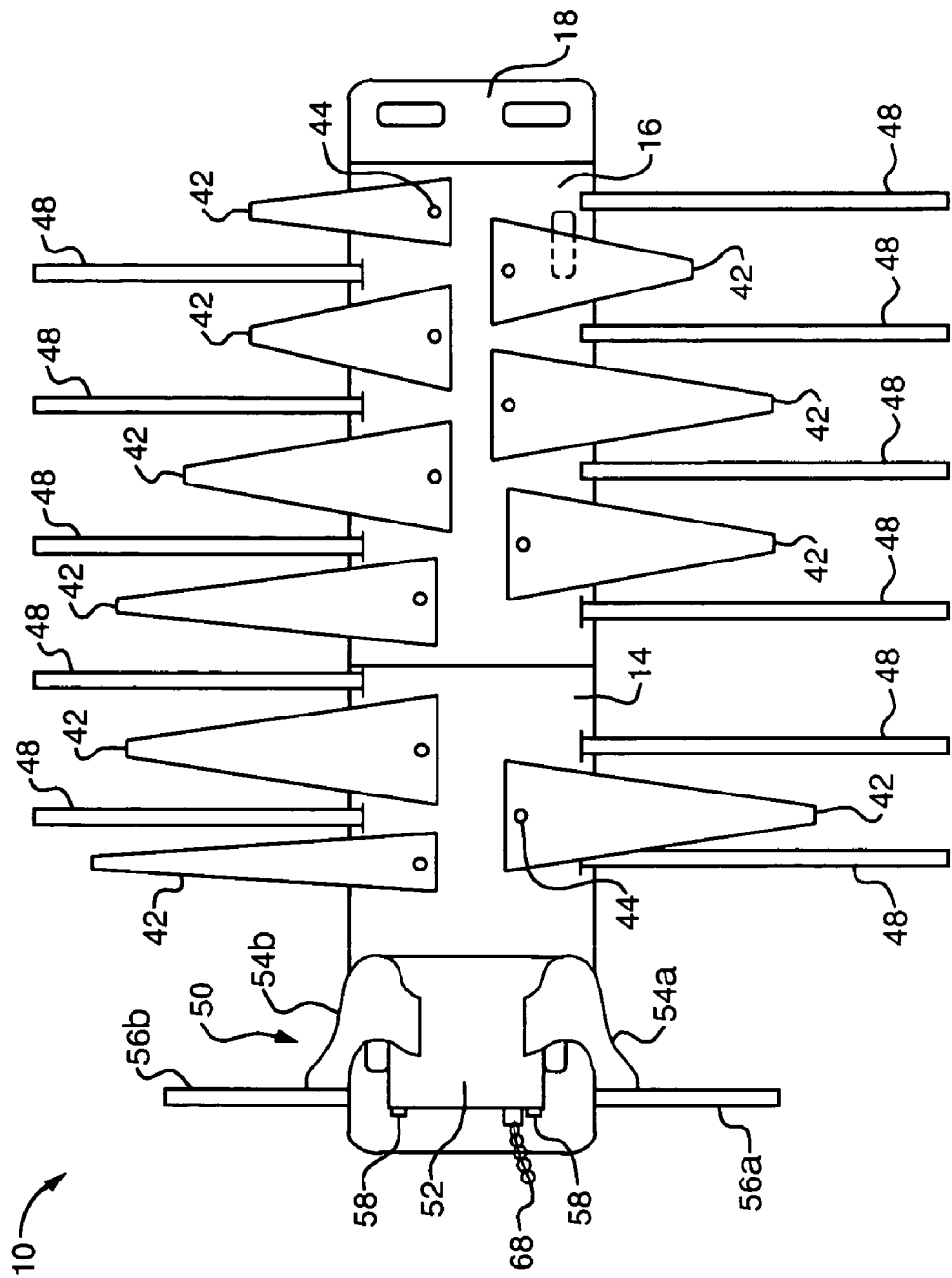
FIG. 2 is a top view of the rescue device showing a plurality of restraining devices and the head gear portion.

FIG. 2 illustrates a plurality of restraining devices used to secure a victim to the device 10. Although a variety of restraining devices may be used, in a variety of locations, illustrated in FIG. 2 is a plurality of gores, webs or flaps 42 spaced along the longitudinal axis of the device 10. Gores 42 may be located on both top/head portion 14 and middle/body portion 16, and are preferably spaced in an alternating fashion. Gores 42 are preferably made of a smooth strong plastic or other material which is strong yet flexible and easily kept clean. Gores 42 may be attached in a variety of locations and manners. For example gores 42 may be pivotally attached to device 10 (on top/head portion 14 and/or middle/body portion 16) at points 44 such that each gore 42 may be pivoted and set at a variety of angles with respect to the longitudinal axis of device 10. The ends of gores 42, where they meet and are attached to either top/head portion 14 or middle/body portion 16, may be kept somewhat rigid by thin stiffening members 46, as shown in greater detail in FIG. 4. Gores 42 may alternatively be attached to the underside of removable padding 43 that is used with device 10, as shown in FIG. 4a. The removable padding 43 shown in FIG. 4a could be that used with either top/head portion 14 or middle/body portion 16. If gores 42 are attached to top/head portion 14 and/or middle/body portion 16 padding 43 may be held in place by gores 42 with a victim lying on padding 43. If gores 42 are attached to the padding 43 and secure a victim to the padding, then there may be additional restraining devices such as additional gores 42 attached to top/head portion 14 and middle/body portion 16 to secure both padding 43 and the victim to rescue device 10.

Figure 5:
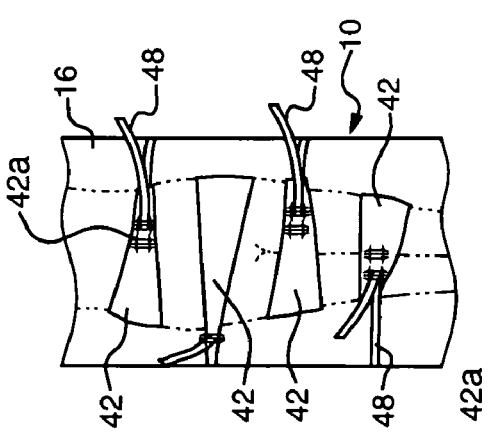
FIG. 5 shows the middle/body section of the device, with a victim secured thereon by the plurality of restraining devices.

Also included may be a plurality of adjustable connecting straps 48. Connecting straps 48 may be used to secure the gores 42 in place once gores 42 are wrapped around a given portion of a victim's body from well under the body (being attached to either top/head portion 14, middle/body portion 16 or the underside of the removable padding on top/head portion 14 and/or middle/body portion 16) and thence up and around the portion of the body being secured, to a point on the opposite edge of device 10. In this manner a tear drop cross section is formed. FIG. 5 illustrates gores 42 wrapped around a portion of a victim's body, secured by straps 48. Because gores 42 are pivotally mounted each gore 42 can follow the respective body contour. Thus, gores 42 can engage and contain the entire body envelope over a considerable surface thereof. In order for gores 42 to be able to be secured in whatever position is needed straps 48 are located in a variety of positions, and not necessarily directly opposite of each gore 42. Therefore, rescue personnel can select an appropriate strap 48 to maximize the supportive affect of each gore 42 and its positioning. Because each gore 42 wraps the victim from a point well under the victim, effective lateral support is also achieved. Thus, should it become necessary to tilt the victim, as is often the case, movement of the body envelope is minimized. As a method of securing gores 42 with straps 48, at least one, and preferably two "D-rings" 42a, as shown in FIG. 5, may be located toward the far end of each gore 42 to accommodate a variety of body sizes. Preferably D-rings 42a are secured to the outside surfaces of gores 42. To fasten straps 48 to gores 42 via D-rings 42a all fastening may be by conventional buckle or other snapping or gripping techniques including hook and loop fastening means such as VELCRO® hook and loop fastening means, or plastic snap and release buckles as commonly found on modern straps of backpacks and the like, or any other means known that provides quick fastening, infinite adjustability, and quick release. For example, straps 48 may be formed from VELCRO® hook and loop fastening means to allow easy adjustment, attachment and release.

Thus, with the combination of gores 42 and straps 48, the body envelope of a victim is effectively immobilized. However, there is still a need for a method of keeping the skeletal structure likewise immobilized within the body envelope. While some movement of bones relative to the skin surface is inevitable by the very nature of the human body, the present invention provides a method and device for minimizing such motion, especially in the case of cervical spine injuries in which the problems associated with skeletal motion are most acute.

Figure 8:
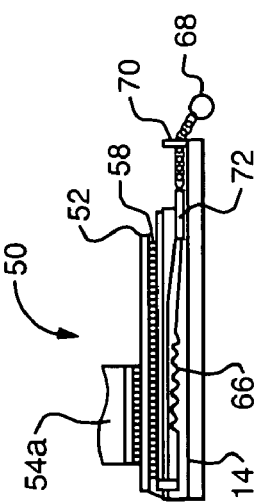
FIG. 8 is a side view illustrating an example of traction application mechanism usable as part of the present invention.
Figure 6:
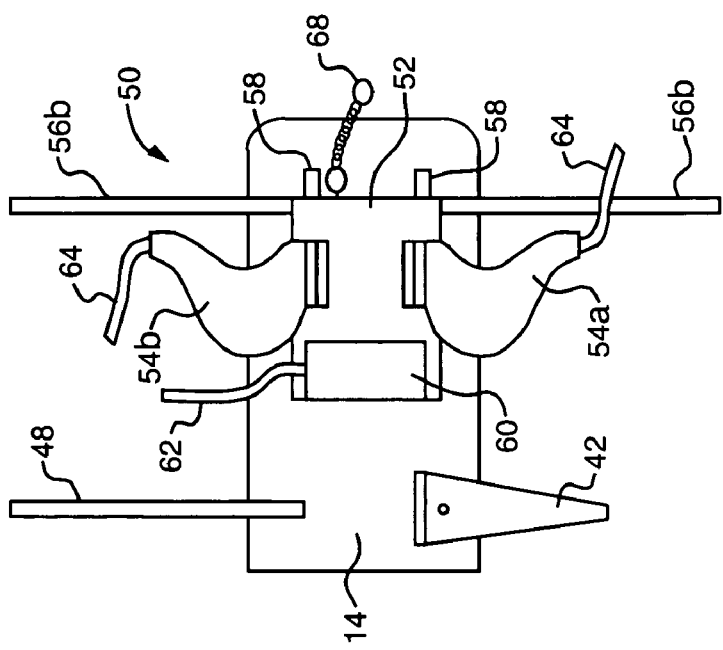
FIG. 6 is a top view of the head gear showing the optional inflatable cervical pillow, head restraint devices and traction application mechanism.
Figure 7:
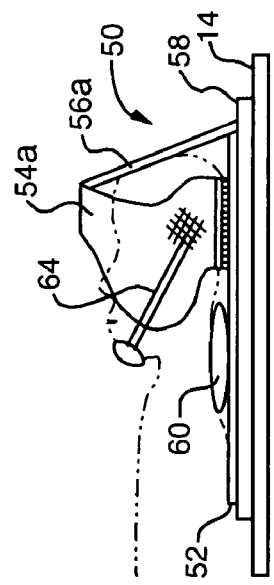
FIG. 7 illustrates the head gear with a victim's head therein, illustrating the use of the cervical pillow and traction mechanism that extends beyond the neck vertebrae.

As shown in FIG. 2, and in greater detail in FIGS. 6, 7, and 8, the invention includes a head gear assembly 50 which comprises a base 52, laterally supporting "wings" 54a and 54b, and straps 56a and 56b that are used to hold lateral supports 54a and 54b in place to stabilize the head. Base 52 is slidably biased along the longitudinal axis of device 10 to permit the victim's head to move, if necessary, as the rest of the skeletal structure moves. Base 52 is mounted preferably on a ball track 58 or similar easily slidable mechanism so that it may move along the longitudinal axis of the device 10. Head gear assembly 50, by way of track 58 is also completely removable from top/head portion 14. The victim's head is placed on base 52, which may have removable padding. Base 52 and track 58 may extend only to the base of the skull, or base 52 and ball track 58 may be formed to extend for several inches below the base of the skull to provide additional support to lower vertebrae, and for example may be formed to extend to the thoracic vertebrae.

If the victim is in the supine position, the cervical arch is supported by a removable inflatable cushion 60 which may be inflated to the desired size to completely fill the space below the cervical arch. Cushion 60 may be inflated via a tube 62 as shown in FIG. 6, and tube 62 may be clamped or tied or a valve may be provided to retain the air in cushion 60. The victim's head is laterally restrained by removably padded lateral support members or "wings" 54a and 54b as shown in detail in FIGS. 2, 6 and 7. Lateral support members 54a and 54b are hingedly attached to base 52. Lateral support members 54a and 54b are held against either side of the head by straps 56a and 56b, which may be attached to support members 54a and 54b respectively. In addition, a chin strap 64 may be included, as shown in FIG. 7, and used to help maintain proper position of the victim's head on base 52. Chin strap 64 as shown may be conveniently affixed to each support member 54a and 54b by a hook and loop fastening means such as VELCRO® hook and loop fastening means, or other type fastener.

Also included as part of head gear assembly 50 is a spring or other mechanism by which tension can be applied to head gear assembly, and thus traction applied to the head of a victim. Such traction can be provided by way of spring mechanism 66 as shown in FIGS. 6 and 8. In an unused or stored position base 52 is held in a fixed position along track 58 by any known pin type mechanism (not shown) engaging ball track 58 such that base can not move. However, once the pin-type mechanism is removed base 52 is freely slidable or floatable along ball track 58, and is thus in this way is also completely removable from track 58 and top/head portion 14.

In use however, for example, after the victim is secured on device 10 and the head secured on head gear assembly 50, traction can be applied by spring 66. Base 52 must be released by removal of the pin-type device from track 58. A pull chain 68 provides a series of small steps of adjustment by which the tension may be increased or decreased as chain 68 engages a clamp 70. If pin-type device is removed and chain 68 is not pulled and therefore no tension is put on spring 66 head gear assembly 50 moves freely along the longitudinal axis of device 10 along track 58. If the pin-type device is in place in track 58, pulling on chain 68 is ineffective, the chain can not be pulled. While complete immobilization, and no movement at all is not ideal for a victim secured to a rescue device, having unrestricted longitudinal motion of the head is also not optimal.

Putting tension on spring 66, i.e. pulling chain 68 with no pin in track 58, thus slides base 52 along track 58 to a desired location where chain 68 is then clamped in place. This mechanism significantly limits the motion of head gear assembly 50 such that head gear assembly 50, and thus the victim's head secured therein, move only minimally and only in response to movements of the victim's body—in proportion to the strength of the spring 66 and weight of the body and thus the force exerted against the spring 66 by the body. Chain 68 is pulled to the extent/tension desired, and then clamped in place by clamp 70. Thus, in this way, "dynamic" traction, traction/tension that still allows minimal proportional movement is provided.

A spring tension indicator 72 may optionally be placed in series with spring 66 to give readings directly in force units such as pounds. Alternatively, an indicator need not be provided or used if a spring 66 is used which produces, for example, a maximum of five (5) pounds of tractive force. Thus, no more than a given (in this example 5 pounds) amount of force could be applied. Such an amount is generally considered to be below a safe maximum to use under first aid conditions, but whatever is determined by the user to be a safe strength of spring and/or means of reading tension as desired could be used. However, it should be emphasized that under emergency conditions, the traction supplied by rescuers using the present invention may not be that which would be ultimately prescribed after clinical diagnosis. What the present invention provides is simply sufficient traction to keep a victim's head and body in a fixed relationship during transport. Thus, generally only a few pounds of traction are required for such a purpose, as too much traction might be medically excessive. However, the present invention does provide dynamic traction, that is, within the skeletal movements that are to be inevitably expected during rescue and transport of a victim, the "follow up" movements allowed by the head gear assembly 50 keep constant the spatial relationship between the head and spine. Devices that immobilize the head in a particular position with respect to the spine provide static traction and while immobilizing the head, do not allow the head to move with the spine, and may cause further injury or exacerbate existing injury.

Thus, with the present invention a victim can be maintained in the dynamic traction relationship as long as necessary to ultimately diagnose and treat the victim, thus preventing or minimizing further injury during rescue and transport.

In summary, the main features of the invention, and improvements over prior stretcher devices are:

Portablilty—the device of the present invention can be disassembled and thus stored and carried in a much smaller space than traditional stretchers. For example ambulances can carry two of the devices of the invention, and thus have two full length and two short board stretcher devices available, rather than the current situation in which ambulances are required to carry both a "short board" and a "long board" and thus do not have room to carry two of each. With the present invention, in a smaller space one can store and carry essentially two short boards and two long boards. In addition, because the present invention is "collapsible" and disassemblable, it can be packaged to be carried hands-free if desired, for example in a back-pack type assembly to be carried by, for example, a military medic, possibly jumping out of an aircraft. Other uses and advantages of the portability and convertibility of the present invention will be obvious to those of skill in the art.

Removably Padded—with the padding for both the top/head portion and the padding for the middle/body portion being removable, the padding can be easily stored and carried separately from the rigid top/head, middle/body, and optional bottom/foot portions. Additionally, because the padding is removable it is easily cleaned, which is a distinct advantage and necessity with today's modern health concerns.

Various design characteristics—the basic design of the present invention can be modified and adapted to a variety of applications such as for ski rescue in which stretcher devices of the traditional 18 inch width are too wide to fit in a rescue sled. A device of the present invention can easily be made in a width of about 16 inches or even less depending on the application desired. As an additional example, some military rescue situations may require a narrower width—for example to fit through the scuttle openings on ships, or to be more easily carried by medics and/or in aircraft. The length of the top/head, middle/body and optional bottom/foot portions could also be adjusted when manufactured, to suit a particular application. In addition, all materials of the present invention are preferably formed from a radiolucent material such that only the device of the invention need be used in all steps from immediate rescue to transport to x-ray upon arrival at a medical facility.

While the present invention has been described by particular examples herein, the examples provided are merely illustrative of the various forms and applications of the present invention and are in no way limiting. It is apparent to those of skill in the art that various additions and modifications can be made thereto, and various alternatives in size, shape and materials can be selected, without departing from the scope and spirit of the invention as described herein and illustrated by the accompanying drawing figures and detailed description.

What is claimed is:

1. A rescue device comprising:

A top portion having a first head end and a second end, and a middle portion having a first end and a second end, said second end of said top portion being connectable longitudinally to said first end of said middle portion to form a single device;

A plurality of restraining devices attached to said top portion and said middle portion;

A removable head gear portion attachable to and slidably adjustable longitudinally along said top portion;

A bottom portion attachable longitudinally to said middle portion, at said second end of said middle portion; and Removable padding positionable on said top portion and said middle portion.

2. The rescue device of claim 1 wherein said top portion, said middle portion and said bottom portion are comprised of a radiolucent material.

3. The rescue device of claim 1 wherein said top portion, said middle portion and said bottom portion are injection molded.

4. The rescue device of claim 3 wherein said top portion, said middle portion and said bottom portion are hollow and have a foam core therein.

5. The rescue device of claim 1 comprising at least one hand hold means on each of said top portion and said middle portion.

6. The rescue device of claim 1 comprising at least one hand hold means on said bottom portion.

7. The rescue device of claim 1 wherein said top portion comprises two laterally spaced edges, each of which has thereon an attachment extension; and wherein said middle portion comprises two laterally spaced edges, each of which has thereon an attachment receiver that interfits with a corresponding said attachment extension of said top portion to attach said top portion and said middle portion together.

8. The device of claim 1 wherein said bottom portion comprises two laterally spaced edges, along each of which is an attachment extension; and wherein said middle portion comprises two laterally spaced edges, along each of which is an attachment receiver that interfits with a corresponding said attachment extension of said bottom portion to attach said middle portion and said bottom portion together.

9. The device of claim 1 wherein said top portion comprises an underside comprising at least one elevation means disposed longitudinally along said underside.

10. The device of claim 9 wherein said elevation means comprises at least one telescoping rail device extendable along the length of said top portion.

11. The device of claim 10 comprising at least one lock or clamp disposed on said underside of said top portion, into which a distal end of each said at least one telescoping rail device is insertable and by which each said at least one telescoping rail device is maintained in an extended position.

12. The device of claim 10 comprising a spring locking means having at least one spring-actuated means having a normally-compressed spring, located at the proximal end of the last or distal said telescoping member of each said at least one telescoping rail device and at least one corresponding mating aperture at a distal end of the penultimate said telescoping member of each said at least one telescoping rail device, such that when each said telescoping rail device is extended, each said at least one spring-actuated means becomes aligned with a corresponding mating aperture and, by way of said normally-compressed spring, extends through said aperture, thus locking said telescoping rail device in an extended position until released by pressing on each said at least one spring-actuated means to compress said normally-compressed spring and unlock each said at least one rail device.

13. The device of claim 9 wherein said elevation means comprises at least one telescoping rail device, comprising multiple telescoping members, attached to either said top portion or said middle portion, and extendable along the combined length of said top portion and said middle portion.

14. The device of claim 13 comprising at least one track device disposed longitudinally along said underside of said top portion and said underside of said middle portion along which said at least one telescoping rail device extends and by which said at least one telescoping rail device is held in place.

15. The device of claim 13 comprising at least one lock or clamp disposed on said underside of either said top portion or said middle portion into which a distal end of each said telescoping rail device is insertable and by which each said at least one telescoping rail device is maintained in an extended position.

16. The device of claim 13 comprising a spring locking means having at least one spring-actuated means having a normally-compressed spring, located at the proximal end of the last or distal said telescoping member of each said at least one telescoping rail device and at least one corresponding mating aperture at a distal end of the penultimate said telescoping member of each said at least one telescoping rail device, such that when each said telescoping rail device is extended, each said at least one spring-actuated means becomes aligned with a corresponding mating aperture and, by way of said normally-compressed spring, extends through said aperture, thus locking said telescoping rail device in an extended position until released by pressing on each said at least one spring-actuated means to compress said normally-compressed spring and unlock each said at least one rail device.

17. The device of claim 10 comprising at least one track device disposed longitudinally along said underside of said top portion along which said at least one telescoping rail device extends and by which said at least one telescoping rail device is held in place.

18. The device of claim 9 wherein said elevation means comprises at least one fixed rail device formed as part of said top portion.

19. The device of claim 1 wherein said middle portion comprises an underside comprising at least one elevation means disposed longitudinally along said underside.

20. The device of claim 19 wherein said elevation means comprises at least one fixed rail device formed as part of said middle portion.

21. The device of claim 19 wherein said elevation means comprises at least one telescoping rail device comprising multiple telescoping members extendable along the length of said middle portion.

22. The device of claim 21 comprising at least one track device disposed longitudinally along said underside of said middle portion along which said at least one telescoping rail device extends and by which said at least one telescoping rail device is held in place.

23. The device of claim 21 comprising at least one lock or clamp disposed on said underside of said middle portion, into which a distal end of each said at least one telescoping rail device is insertable and by which each said at least one telescoping rail device is maintained in an extended position.

24. The device of claim 21 comprising a spring locking means having at least one spring-actuated means having a normally-compressed spring, located at the proximal end of the last or distal said telescoping member of each said at least one telescoping rail device and at least one corresponding mating aperture at a distal end of the penultimate said telescoping member of each said at least one telescoping rail device, such that when each said telescoping rail device is extended, each said at least one spring-actuated means becomes aligned with a corresponding mating aperture and, by way of said normally-compressed spring, extends through said aperture, thus locking said telescoping rail device in an extended position until released by pressing on each said at least one spring-actuated means to compress said normally-compressed spring and unlock each said at least one rail device.

25. The device of claim 1 wherein said bottom portion comprises an underside comprising at least one elevation means disposed longitudinally along said underside.

26. The device of claim 25 wherein said elevation means comprises at least one fixed rail device formed as part of said bottom portion.

27. The device of claim 1 wherein said restraining devices are chosen from the group consisting of: gores, webs, flaps and straps.

28. The device of claim 27 wherein said top portion and said middle portion each comprise two parallel side edges, parallel to which said restraining devices are disposed.

29. The device of claim 28 wherein a plurality of said restraining devices is spaced in an alternating pattern along and parallel to said two side edges of said top portion and said middle portion.

30. The device of claim 28 wherein said restraining devices are pivotably attached to an upper surface of said top portion and said middle portion at a point inwardly of said side edges of said top portion and said middle portion.

31. The device of claim 27 wherein said restraining devices are comprised of a plastic or nylon material.

32. The device of claim 27 wherein a plurality of said restraining devices is attached to said removable padding.

33. The device of claim 27 wherein said restraining devices are attached to both said top portion and said middle portion, and also to said removable padding.

34. The device of claim 27 comprising a plurality of adjustable connecting means to connect and secure said restraining devices about a body.

35. The device of claim 34 wherein said adjustable connecting means are attached to said top and said middle portions and are spaced along and parallel to said parallel side edges of said top and said middle portions.

36. The device of claim 34 wherein said restraining devices comprise at least one securing means attached thereto for receiving a said adjustable connecting means.

37. The device of claim 36 wherein said at least one securing means comprises a D or O ring device attached to an outer surface of each said restraining device.

38. The device of claim 34 wherein said fastening means is chosen from the group consisting of: hook and loop fastening means, buckle, snap, tie, and snap and release buckle means.

39. The device of claim 1 wherein said removable head gear portion comprises:

A slidable base having pivotable removably padded laterally head-supporting wings, and wing securing means.

40. The device of claim 39 wherein said wing securing means comprise a plurality of strap devices mounted on said top portion or on said head-supporting wings.

41. The device of claim 39 comprising a chin supporting means.

42. The device of claim 41 wherein said chin supporting means comprises a chin strap attachable to said head-supporting wings.

43. The device of claim 39 comprising a removable cervical support, placable to fill the space below the cervical arch of the neck of a victim.

44. The device of claim 43 wherein said removable cervical support comprises an inflatable cushion.

45. The device of claim 44 comprising at least one closable inflation tube by which said inflatable cushion is inflatable.

46. The device of claim 44 comprising an inflation valve by which said inflatable cushion is inflatable.

47. The device of claim 39 wherein said base is slidably mounted on a base-receiving means mounted on said top portion.

48. The device of claim 47 wherein said head gear portion is slidable longitudinally relative to said top portion, and is completely removable from said top portion.

49. The device of claim 47 wherein said base-receiving means extends along the entire length of said top portion.

50. The device of claim 47 wherein said base-receiving means extends along half or more of the length of said top portion.

51. The device of claim 47 wherein said base-receiving means comprises a ball track into which said base is slidably and removably mountable.

52. The device of claim 51 comprising a releaseable head gear locking means which interacts with said base and said base-receiving means to allow or prevent sliding of said base along said base-receiving means.

53. The device of claim 52 wherein said releaseable head gear locking means is a removable pin device insertable along said base-receiving means to lock said base in a fixed position.

54. The device of claim 53 comprising an actuation means attached to said tensioning means for actuating said tensioning means.

55. The device of claim 54 wherein said actuation means comprises a pull-chain device that, when pulled, and when said pin device is removed, exerts force on said tensioning means to slide said base along said base-receiving means to a desired location and tension, and further comprises a clamp means which is engagable with said base and said base-receiving means to maintain said base in an essentially fixed position under a desired amount of tension.

56. The device of claim 47 wherein said head gear portion comprises a traction-providing tensioning means attachable to said base-receiving means.

57. The device of claim 56 wherein said traction-providing tensioning means comprises at least one spring device.

58. The device of claim 56 wherein said head gear portion comprises a tension indicator attachable to said tensioning means and providing readings in force units.

* * * * *